US011579684B1

United States Patent
Arechiga et al.

(10) Patent No.: US 11,579,684 B1
(45) Date of Patent: Feb. 14, 2023

(54) SYSTEM AND METHOD FOR AN AUGMENTED REALITY GOAL ASSISTANT

(71) Applicant: TOYOTA RESEARCH INSTITUTE, INC., Los Altos, CA (US)

(72) Inventors: Nikos Arechiga, San Mateo, CA (US); Shabnam Hakimi, San Francisco, CA (US); Charlene C. Wu, San Francisco, CA (US); Matthew Len Lee, Mountain View, CA (US)

(73) Assignee: TOYOTA RESEARCH INSTITUTE, INC., Los Altos, CA (US)

( * ) Notice: Subject to any disclaimer, the term of this patent is extended or adjusted under 35 U.S.C. 154(b) by 0 days.

(21) Appl. No.: 17/480,841

(22) Filed: Sep. 21, 2021

(51) Int. Cl.
*G06F 3/01* (2006.01)
*G06T 19/00* (2011.01)
*G06F 3/16* (2006.01)
*G06F 3/0481* (2022.01)
*G06V 20/00* (2022.01)

(52) U.S. Cl.
CPC .......... *G06F 3/011* (2013.01); *G06F 3/0481* (2013.01); *G06F 3/167* (2013.01); *G06T 19/006* (2013.01); *G06V 20/00* (2022.01)

(58) Field of Classification Search
CPC .......... A61M 21/02; A61M 2021/0027; A61M 2021/0044; A61M 2205/3303; A61M 2205/3553; A61M 2205/3584; A61M 2205/52; G06F 3/011
See application file for complete search history.

(56) References Cited

U.S. PATENT DOCUMENTS

| | | | |
|---|---|---|---|
| 10,671,151 B2 | 6/2020 | Bastide et al. | |
| 10,719,992 B2 | 7/2020 | Samec et al. | |
| 10,736,544 B2 | 8/2020 | Cramer | |
| 10,761,597 B2 * | 9/2020 | Xu | G06F 3/011 |
| 2016/0077547 A1 * | 3/2016 | Aimone | A61B 5/369 345/8 |
| 2017/0037839 A1 | 11/2017 | Yudofsky et al. | |
| 2018/0254097 A1 | 9/2018 | Gani et al. | |
| 2019/0388647 A1 * | 12/2019 | Bender | A61M 21/02 |
| 2020/0120375 A1 | 4/2020 | Hamon | |

FOREIGN PATENT DOCUMENTS

CN 107000210 A 8/2017

OTHER PUBLICATIONS

Herman, Barbara, "Do Augmented Reality Experiences Change Behavior?", https://www.rga.com/futurevision/pov/do-augmented-realityexperiences-change-behavior, May 16, 2019.

* cited by examiner

*Primary Examiner* — Nelson M Rosario
(74) *Attorney, Agent, or Firm* — Seyfarth Shaw LLP

(57) ABSTRACT

A method for an augmented reality goal assistant is described. The method includes detecting an object associated with a behavioral goal of a user. The method also includes altering an appearance of the object based on the behavioral goal of the user. The method further includes displaying the altered appearance of a detected object on an augmented reality headset, such that the altered appearance of the detected object is modified based on the behavioral goal of the user.

18 Claims, 6 Drawing Sheets

SYSTEM AND METHOD FOR AN AUGMENTED REALITY GOAL ASSISTANT

BACKGROUND

Field

Certain aspects of the present disclosure generally relate to machine learning and, more particularly, to a system and method for an augmented reality goal assistant.

Background

Many people find themselves in real-world situations in which attaining a goal involves changing a behavior in a way that expends willpower. As described, ego depletion refers to the idea that self-control or willpower draws upon a limited pool of mental resources that may be eventually depleted. Behavioral science studies in the phenomenon of ego depletion indicate that such expenditures of willpower are difficult to sustain, and may take a toll on other areas of life that involve willpower. For example, resisting the temptation to eat an unhealthy snack may reduce available willpower to later exercise.

Previous work in goal attainment involved behavioral science incentives to increase behaviors. For example, in one case these behavioral science incentives involved providing gamified rewards, and in another case behavioral science incentives involved providing penalties for non-adherence. Unfortunately, these behavioral science incentives still cause the user to expend willpower for adhering to the desired behavior. A technique for intervening at the sensory level, so that the user is never even conscious of alternatives to deviate from pursuing their intended goal, is desired. In particular, a technique that leverages advanced computer vision techniques and augmented reality technologies to completely circumvent willpower, is desired.

SUMMARY

A method for an augmented reality goal assistant is described. The method includes detecting an object associated with a behavioral goal of a user. The method also includes altering an appearance of the object based on the behavioral goal of the user. The method further includes displaying the altered appearance of a detected object on an augmented reality headset, such that the altered appearance of the detected object is modified based on the behavioral goal of the user.

A non-transitory computer-readable medium having program code recorded thereon for an augmented reality goal assistant is described. The program code is executed by a processor. The non-transitory computer-readable medium includes program code to detect an object associated with a behavioral goal of a user. The non-transitory computer-readable medium also includes program code to alter an appearance of the object based on the behavioral goal of the user. The non-transitory computer-readable medium further includes program code to display the altered appearance of a detected object on an augmented reality headset, such that the altered appearance of the detected object is modified based on the behavioral goal of the user.

A system for an augmented reality goal assistant is described. The system includes an object recognition module to detect an object associated with a behavioral goal of a user. The system also includes an object alteration module to alter an appearance of the object based on the behavioral goal of the user. The system further includes an augmented reality display module to display the altered appearance of a detected object on an augmented reality headset, such that the altered appearance of the detected object is modified based on the behavioral goal of the user.

This has outlined, rather broadly, the features and technical advantages of the present disclosure in order that the detailed description that follows may be better understood. Additional features and advantages of the present disclosure will be described below. It should be appreciated by those skilled in the art that this present disclosure may be readily utilized as a basis for modifying or designing other structures for carrying out the same purposes of the present disclosure. It should also be realized by those skilled in the art that such equivalent constructions do not depart from the teachings of the present disclosure as set forth in the appended claims. The novel features, which are believed to be characteristic of the present disclosure, both as to its organization and method of operation, together with further objects and advantages, will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

The features, nature, and advantages of the present disclosure will become more apparent from the detailed description set forth below when taken in conjunction with the drawings in which like reference characters identify correspondingly throughout.

DETAILED DESCRIPTION

Figure 1:
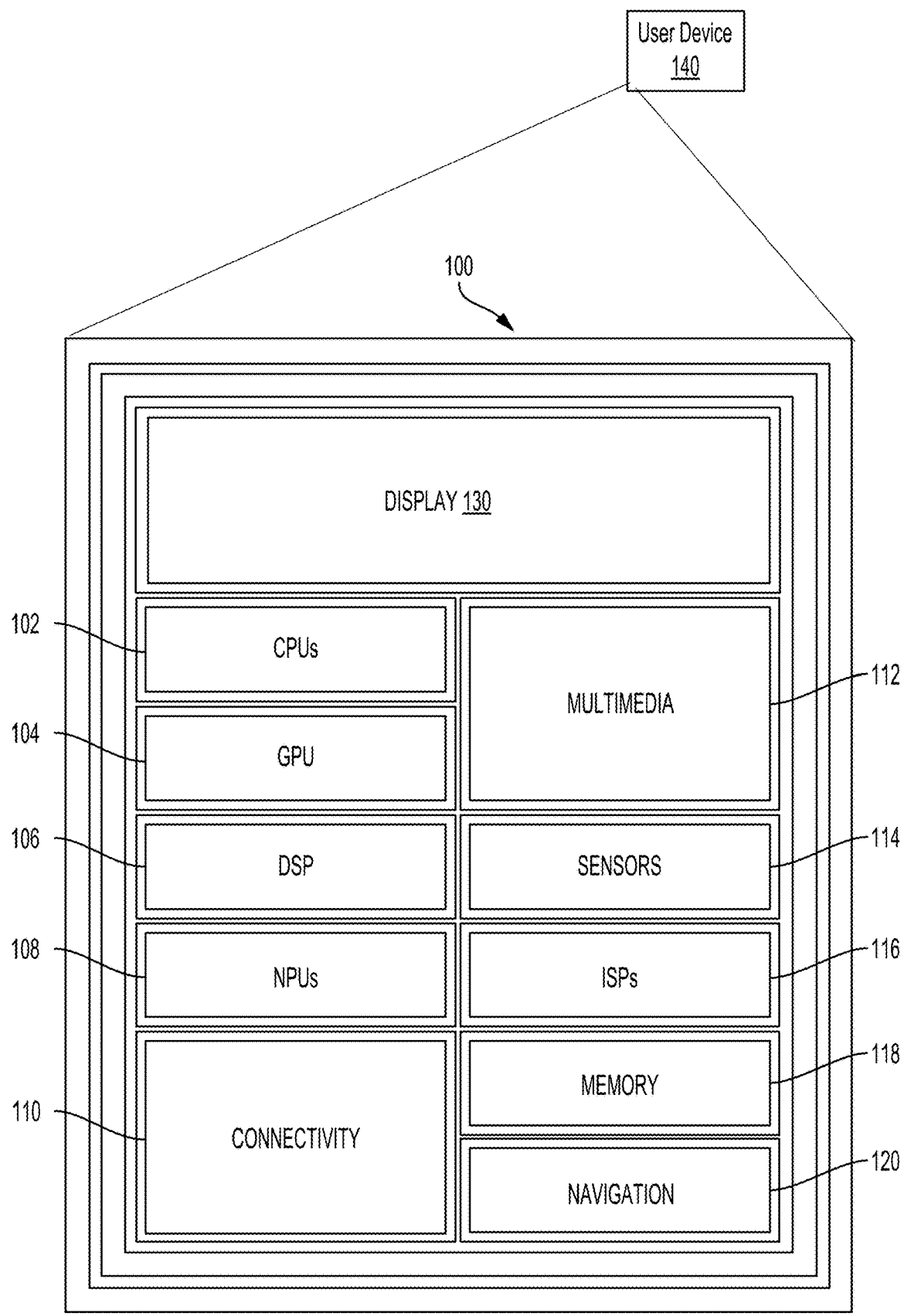
FIG. 1 illustrates an example implementation of designing a neural network using a system-on-a-chip (SOC) of an augmented reality goal assistance system, in accordance with aspects of the present disclosure.

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. It will be apparent to those skilled in the art, however, that these concepts may be practiced without these specific details. In some instances, well-known structures and components are shown in block diagram form in order to avoid obscuring such concepts.

Based on the teachings, one skilled in the art should appreciate that the scope of the present disclosure is intended to cover any aspect of the present disclosure, whether implemented independently of or combined with any other aspect of the present disclosure. For example, an apparatus may be implemented or a method may be practiced using any number of the aspects set forth. In addition, the scope of the present disclosure is intended to cover such an apparatus or method practiced using other structure, functionality, or structure and functionality in addition to, or other than the various aspects of the present disclosure set forth. It should be understood that any aspect of the present disclosure disclosed may be embodied by one or more elements of a claim.

Although particular aspects are described herein, many variations and permutations of these aspects fall within the scope of the present disclosure. Although some benefits and advantages of the preferred aspects are mentioned, the scope of the present disclosure is not intended to be limited to particular benefits, uses, or objectives. Rather, aspects of the present disclosure are intended to be broadly applicable to different technologies, system configurations, networks, and protocols, some of which are illustrated by way of example in the figures and in the following description of the preferred aspects. The detailed description and drawings are merely illustrative of the present disclosure, rather than limiting the scope of the present disclosure being defined by the appended claims and equivalents thereof.

The world is filled with temptations. Consequently, many people find themselves in real-world situations in which attaining a goal involves changing a behavior in a way that expends willpower. As described, ego depletion refers to the idea that self-control or willpower draws upon a limited pool of mental resources that are eventually depleted. Behavioral science studies in this phenomenon of ego depletion indicate that such expenditures of willpower are difficult to sustain, and may take a toll on other areas of life that involve willpower. For example, resisting the temptation to eat an unhealthy snack may reduce available willpower to later exercise.

Previous work in goal attainment involved behavioral science incentives to increase behaviors. For example, in one case these behavioral science incentives involved providing gamified rewards. In another case, behavioral science incentives involved providing penalties for non-adherence. Unfortunately, these behavioral science incentives still cause the user to expend willpower for adhering to the desired behavior. A technique for intervening at the sensory level, so that the user is never even conscious of alternatives to deviate from pursuing their intended goal, is desired. In particular, a technique that leverages advanced computer vision techniques and augmented reality technologies to completely circumvent willpower, is desired.

Some aspects of the present disclosure leverage an augmented reality headset together with advanced semantic segmentation of images and understanding of audio to modify the sensory inputs a human perceives. In this aspect of the present disclosure, a user accesses a web application interface to highlight types of everyday objects that should be highlighted or hidden. Next, the user wears an augmented reality headset that automatically highlights or hides the relevant everyday objects. This allows the human to control their sensory cues, increasing the salience of cues that increase the behavior of interest and damping or removing cues that cause the behavior they want to omit. In this way, a user can more easily adhere to desired behaviors that allow them to achieve their goals, with minimal expenditure of willpower.

Some aspects of the present disclosure measure the strength of the habit being formed (e.g, duration without performing undesired behavior, number of instances of positive behavior, etc.) to determine whether a habit is stable. For example, in response to a stable habit (which can be a protective factor), the system may selectively reveal stimuli that may trigger the undesired behavior to bring the user slowly back into a realistic view of the world. These aspects of the present disclosure dynamically adapt the degree to which the system hides or highlights objects in the environment depending on the user's past behaviors.

FIG. 1 illustrates an example implementation of the aforementioned system and method for an augmented reality goal assistance system using a system-on-a-chip (SOC) 100, according to aspects of the present disclosure. The SOC 100 may include a single processor or multi-core processors (e.g., a central processing unit (CPU) 102), in accordance with certain aspects of the present disclosure. Variables (e.g., neural signals and synaptic weights), system parameters associated with a computational device (e.g., neural network with weights), delays, frequency bin information, and task information may be stored in a memory block. The memory block may be associated with a neural processing unit (NPU) 108, a CPU 102, a graphics processing unit (GPU) 104, a digital signal processor (DSP) 106, a dedicated memory block 118, or may be distributed across multiple blocks. Instructions executed at a processor (e.g., CPU 102) may be loaded from a program memory associated with the CPU 102 or may be loaded from the dedicated memory block 118.

The SOC 100 may also include additional processing blocks configured to perform specific functions, such as the GPU 104, the DSP 106, and a connectivity block 110, which may include fourth generation long term evolution (4G LTE) connectivity, unlicensed Wi-Fi connectivity, USB connectivity, Bluetooth® connectivity, and the like. In addition, a multimedia processor 112 in combination with a display 130 may, for example, select a control action, according to the display 130 illustrating a view of a user device.

In some aspects, the NPU 108 may be implemented in the CPU 102, DSP 106, and/or GPU 104. The SOC 100 may further include a sensor processor 114, image signal processors (ISPs) 116, and/or navigation 120, which may, for instance, include a global positioning system. The SOC 100 may be based on an Advanced Risk Machine (ARM) instruction set or the like. In another aspect of the present disclosure, the SOC 100 may be a server computer in communication with a user device 140. In this arrangement, the user device 140 may include a processor and other features of the SOC 100.

In this aspect of the present disclosure, instructions loaded into a processor (e.g., CPU 102) or the NPU 108 of the user device 140 may include code to generate an augmented reality goal assistant. The instructions loaded into a processor (e.g., CPU 102) may also include code to detect an object associated with a behavioral goal of a user. The instructions loaded into a processor (e.g., CPU 102) may also include code to alter an appearance of the detected object based on the behavioral goal of the user. The instructions loaded into a processor (e.g., CPU 102) may also include code to display an altered appearance of the detected object on an augmented reality headset, such that the altered appearance of the detected object is modified based on the behavioral goal of the user.

Figure 2:
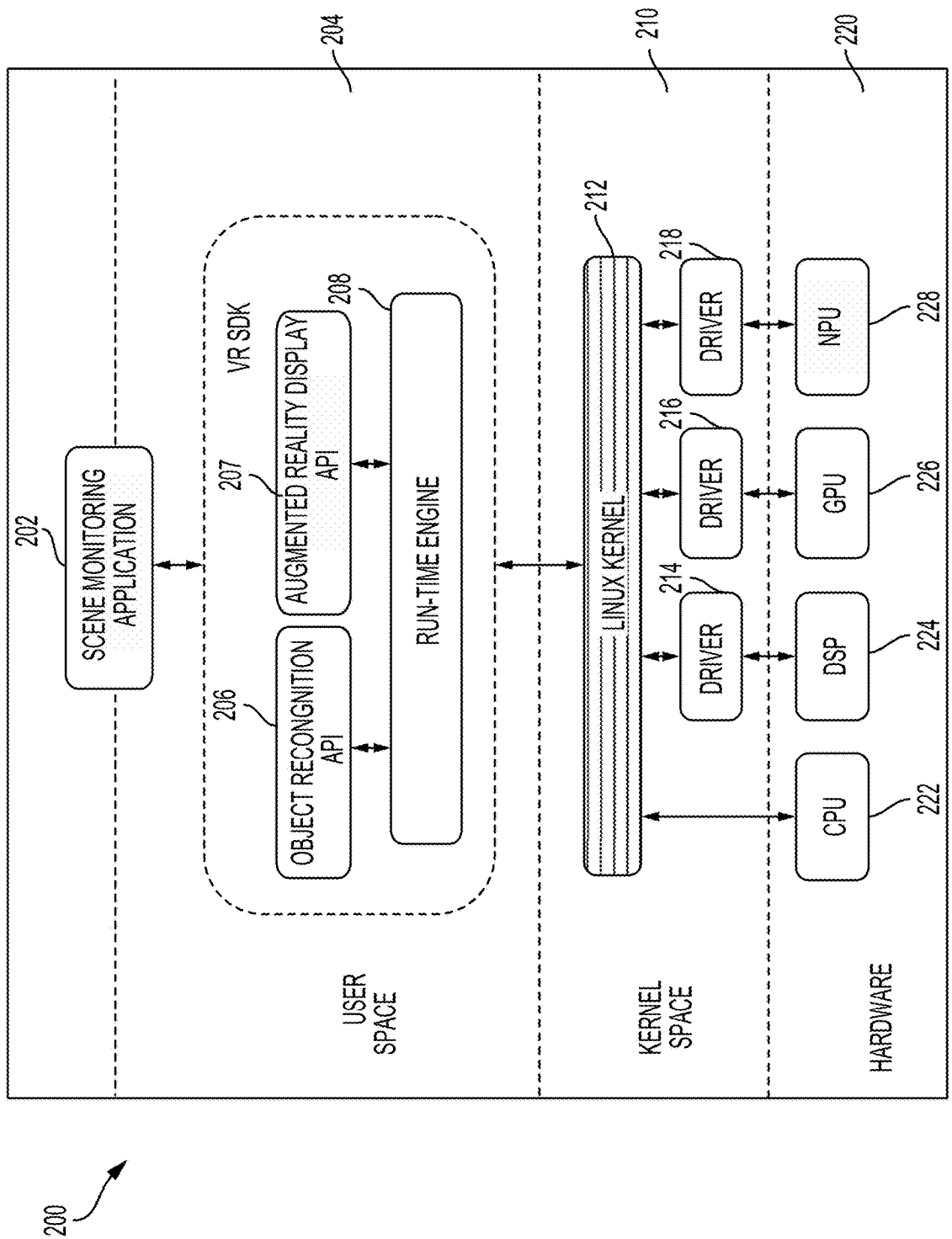
FIG. 2 is a block diagram illustrating an exemplary software architecture that may modularize artificial intelligence (AI) functions of augmented reality for a goal assistance system, according to aspects of the present disclosure.

FIG. 2 is a block diagram illustrating a software architecture 200 that may modularize artificial intelligence (AI) functions for an augmented reality goal assistance system, according to aspects of the present disclosure. Using the architecture, a scene monitoring application 202 may be designed such that it may cause various processing blocks of an SOC 220 (for example a CPU 222, a DSP 224, a GPU 226, and/or an NPU 228) to perform supporting computations during run-time operation of the scene monitoring application 202. FIG. 2 describes the software architecture 200 for the augmented reality goal assistance system. It should be recognized that the augmented reality goal assistance system is not limited to achieving user goals. According to aspects of the present disclosure, the augmented reality goal assistant is applicable to enforcing and/or encouraging or discouraging any type of user behavior.

The scene monitoring application 202 may be configured to call functions defined in a user space 204 that may, for example, provide for goal assistance using an augmented reality display, such as a virtual reality headset. The scene monitoring application 202 may make a request for compiled program code associated with a library defined in an object recognition application programming interface (API) 206. The object recognition API 206 is configured to detect an object associated with a behavioral goal of a user. In addition, the compiled program code of an augmented reality display API 207 is configured to alter an appearance of the object based on the behavioral goal of the user. In response, the compiled program code of the augmented reality display API 207 is configured to display an altered appearance of the detected object on an augmented reality headset, such that the altered appearance of the detected object is modified based on the behavioral goal of the user.

A run-time engine 208, which may be compiled code of a run-time framework, may be further accessible to the scene monitoring application 202. The scene monitoring application 202 may cause the run-time engine 208, for example, to take actions for altering the appearance and displaying the altered appearance of the detected object. In response to interaction with the altered appearance display of the detected object, the run-time engine 208 may in turn send a signal to an operating system 210, such as a Linux Kernel 212, running on the SOC 220. FIG. 2 illustrates the Linux Kernel 212 as software architecture for a goal assistance system using a virtual reality headset. It should be recognized, however, that aspects of the present disclosure are not limited to this exemplary software architecture. For example, other kernels may provide the software architecture to support the augmented reality goal assistance functionality.

The operating system 210, in turn, may cause a computation to be performed on the CPU 222, the DSP 224, the GPU 226, the NPU 228, or some combination thereof. The CPU 222 may be accessed directly by the operating system 210, and other processing blocks may be accessed through a driver, such as drivers 214-218 for the DSP 224, for the GPU 226, or for the NPU 228. In the illustrated example, the deep neural network may be configured to run on a combination of processing blocks, such as the CPU 222 and the GPU 226, or may be run on the NPU 228, if present.

As described, ego depletion refers to the idea that self-control or willpower draws upon a limited pool of mental resources that are eventually depleted. Behavioral science studies in this phenomenon of ego depletion indicate that such expenditures of willpower are difficult to sustain, and may take a toll on other areas of life that involve willpower. For example, resisting the temptation to eat an unhealthy snack may reduce available willpower to later exercise. Unfortunately, the real-world is filled with temptations. Consequently, many people find themselves in real-world situations in which attaining a goal involves changing a behavior in a way that expends willpower to avoid temptation. A technique for intervening at the sensory level, such as a technique that leverages advanced computer vision and augmented reality technologies to completely circumvent willpower, is desired.

Some aspects of the present disclosure leverage an augmented reality headset together with advanced semantic segmentation of images and understanding of audio to modify the sensory inputs a human perceives. Some aspects of the present disclosure measure the strength of the habit being formed (e.g, duration without performing undesired behavior, number of instances of positive behavior, etc.) to determine whether a habit is stable. For example, in response to a stable habit (which can be a protective factor), the system may selectively reveal stimuli that may trigger the undesired behavior to bring the user slowly back into a realistic view of the world. These aspects of the present disclosure dynamically adapt the degree to which the system hides or highlights objects in the environment depending on the user's past behaviors.

Figure 3:
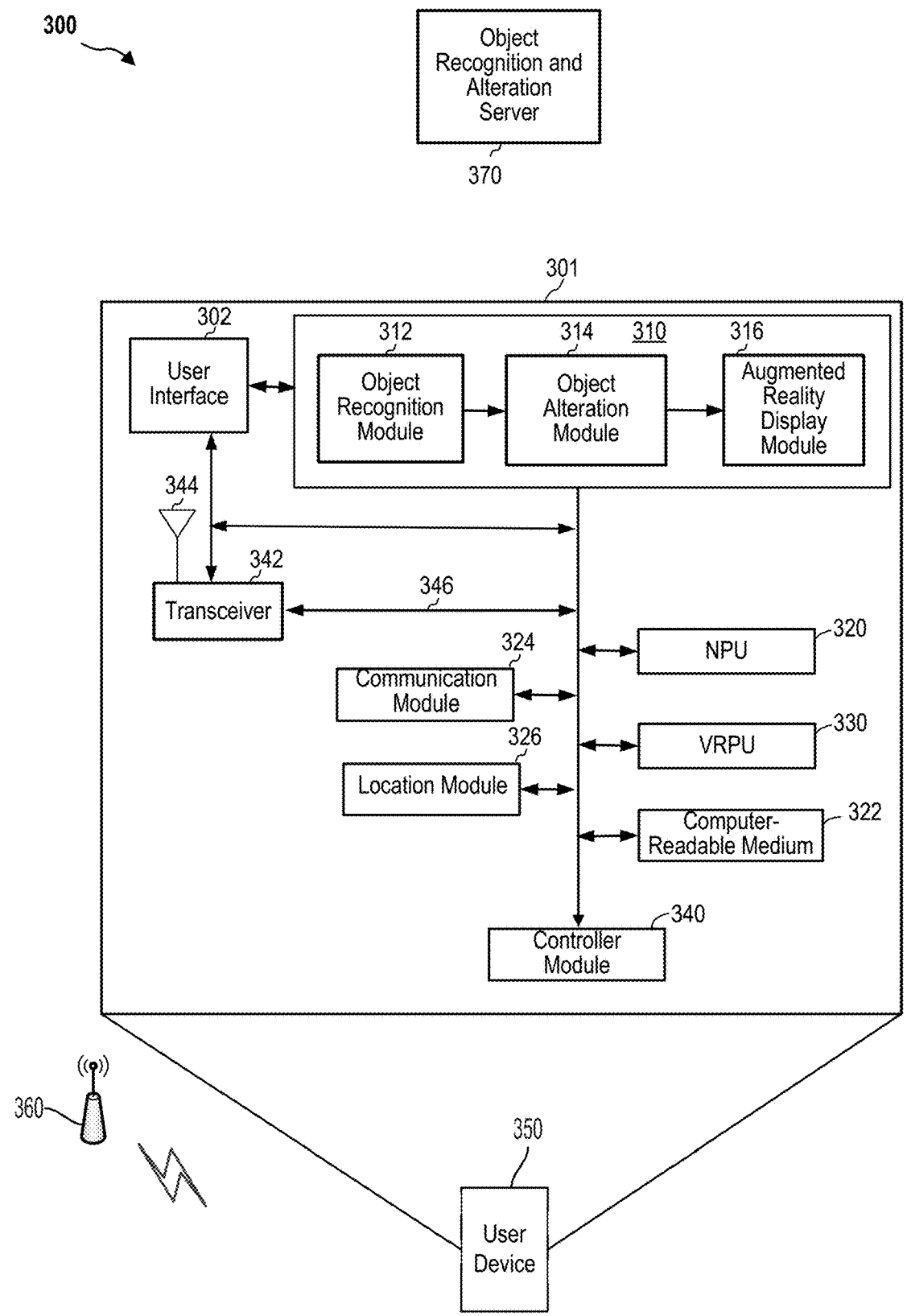
FIG. 3 is a diagram illustrating a hardware implementation of an augmented reality goal assistance system, according to aspects of the present disclosure.

FIG. 3 is a diagram illustrating a hardware implementation for an augmented reality goal assistance system 300, according to aspects of the present disclosure. The augmented reality goal assistance system 300 may be configured to detect an object associated with a behavioral goal of a user. The augmented reality goal assistance system 300 is also configured to alter an appearance of the detected object based on the behavioral goal of the user. In addition, the augmented reality goal assistance system 300 is configured to display an altered appearance of the detected object on an augmented reality headset, such that the altered appearance of the detected object is modified based on the behavioral goal of the user.

The augmented reality goal assistance system 300 includes a user monitoring system 301 and an object recognition and alteration server 370 in this aspect of the present disclosure. The user monitoring system 301 may be a component of a user device 350. The user device 350 may be a cellular phone (e.g., a smart phone), a personal digital assistant (PDA), a wireless modem, a wireless communications device, a handheld device, a laptop computer, a cordless phone, a wireless local loop (WLL) station, a tablet, a camera, a gaming device, a netbook, a smartbook, an ultrabook, a medical device or equipment, biometric sensors/devices, wearable devices (smart watches, smart clothing, smart glasses, smart wrist bands, smart jewelry (e.g., smart ring, smart bracelet)), an entertainment device (e.g., a music or video device, or a satellite radio), a global positioning system device, or any other suitable device that is configured to communicate via a wireless or wired medium.

The object recognition and alteration server 370 may connect to the user device 350 for detecting an object associated with a behavioral goal of the user. For example, the object recognition and alteration server 370 may recognize an object that is associated with a negative behavior avoidance goal of the user. In response, the object recognition and alteration server 370 is configured to alter an appearance of the detected object based on the behavioral goal of the user. In addition, the object recognition and alteration server 370 is configured to transmit an altered appearance of the detected object to an augmented reality headset, such that the altered appearance of the detected object is modified based on the behavioral goal of the user.

The user monitoring system 301 may be implemented with an interconnected architecture, represented generally by an interconnect 346. The interconnect 346 may include any number of point-to-point interconnects, buses, and/or bridges depending on the specific application of the user monitoring system 301 and the overall design constraints. The interconnect 346 links together various circuits including one or more processors and/or hardware modules, represented by a user interface 302, a scene activity module 310, a neutral network processor (NPU) 320, a computer-readable medium 322, a communication module 324, a location module 326, a virtual reality (VR) processing unit (VRPU) 330, and a controller module 340. The interconnect 346 may also link various other circuits such as timing sources, peripherals, voltage regulators, and power management circuits, which are well known in the art, and therefore, will not be described any further.

The user monitoring system 301 includes a transceiver 342 coupled to the user interface 302, the scene activity module 310, the NPU 320, the computer-readable medium 322, the communication module 324, the location module 326, the VRPU 330, and the controller module 340. The transceiver 342 is coupled to an antenna 344. The transceiver 342 communicates with various other devices over a transmission medium. For example, the transceiver 342 may receive commands via transmissions from a user or a connected vehicle. In this example, the transceiver 342 may receive/transmit information for the scene activity module 310 to/from connected devices within the vicinity of the user device 350.

The user monitoring system 301 includes the NPU 320 coupled to the computer-readable medium 322. The NPU 320 performs processing, including the execution of software stored on the computer-readable medium 322 to provide a neural network model for user monitoring and advice recommendation functionality according to the present disclosure. The software, when executed by the NPU 320, causes the user monitoring system 301 to perform the various functions described for presenting an altered, augmented reality display of a recognized object to the user through the user device 350, or any of the modules (e.g., 310, 324, 326, 330, and/or 340). The computer-readable medium 322 may also be used for storing data that is manipulated by the VRPU 330 when executing the software to analyze user communications.

The location module 326 may determine a location of the user device 350. For example, the location module 326 may use a global positioning system (GPS) to determine the location of the user device 350. The location module 326 may implement a dedicated short-range communication (DSRC)-compliant GPS unit. A DSRC-compliant GPS unit includes hardware and software to make the autonomous vehicle 350 and/or the location module 326 compliant with the following DSRC standards, including any derivative or fork thereof: EN 12253:2004 Dedicated Short-Range Communication—Physical layer using microwave at 5.8 GHz (review); EN 12795:2002 Dedicated Short-Range Communication (DSRC)—DSRC Data link layer: Medium Access and Logical Link Control (review); EN 12834:2002 Dedicated Short-Range Communication—Application layer (review); EN 13372:2004 Dedicated Short-Range Communication (DSRC)—DSRC profiles for RTTT applications (review); and EN ISO 14906:2004 Electronic Fee Collection—Application interface.

The communication module 324 may facilitate communications via the transceiver 342. For example, the communication module 324 may be configured to provide communication capabilities via different wireless protocols, such as 5G new radio (NR), Wi-Fi, long term evolution (LTE), 4G, 3G, etc. The communication module 324 may also communicate with other components of the user device 350 that are not modules of the user monitoring system 301. The transceiver 342 may be a communications channel through a network access point 360. The communications channel may include DSRC, LTE, LTE-D2D, mmWave, Wi-Fi (infrastructure mode), Wi-Fi (ad-hoc mode), visible light communication, TV white space communication, satellite communication, full-duplex wireless communications, or any other wireless communications protocol such as those mentioned herein.

The user monitoring system 301 also includes the VRPU 330 to present the altered object to the user in virtual reality. From behavioral science, it is recognized that intervening at the sensory level, so that the user is never even conscious of alternatives to deviate from pursuing their intended goal, is desired. As a result, the user monitoring system 301 may allow a human user to interact in virtual reality with an altered presentation of an object associated with a behavioral goal of the user using the VRPU 330. In these aspects of the present disclosure, the scene activity module 310, in conjunction with the VRPU 330, allows a user to interact with an altered appearance of the detected object on an augmented reality headset, such that the altered appearance of the detected object is modified based on the behavioral goal of the user.

The scene activity module 310 may be in communication with the user interface 302, the NPU 320, the computer-readable medium 322, the communication module 324, the location module 326, the VRPU 330, the controller module 340, and the transceiver 342. In one configuration, the scene activity module 310 monitors communications from the user interface 302. The user interface 302 may monitor user communications to and from the communication module 324. According to aspects of the present disclosure, the VRPU 330 may use computer vision techniques to find the boundaries of the graphical object and subsequently decompose the object into its components. For example, the graphical components may include individual data points, lines, bars, or color areas (e.g., in the case of heat maps).

As shown in FIG. 3, the scene activity module 310 includes an object recognition module 312, an object alteration module 314, and an augmented reality display module 316. The object recognition module 312, the object alteration module 314, and the augmented reality display module 316 may be components of a same or different artificial neural network. This configuration of the scene activity module 310 includes the object recognition module 312 configured to detect an object associated with a behavioral goal of the user. In addition, the scene activity module 310 includes the object alteration module 314 configured to alter an appearance of the detected object based on the behavioral goal of the user. In addition, the scene activity module 310 includes the augmented reality display module 316 configured to display an altered appearance of the detected object on an augmented reality headset, such that the altered appearance of the detected object is modified based on the behavioral goal of the user. In some aspects of the present disclosure, the object recognition module 312 may be implemented and/or work in conjunction with the the object recognition and alteration server 370.

In aspects of the present disclosure, the augmented reality goal assistance system 300 relies on augmented reality techniques for assisting individuals in changing certain behaviors. The augmented reality goal assistance system 300 includes an augmented reality (AR) headset (e.g., the user device 350) that can be worn by a user. As the user goes about their daily life, the AR headset can modify what is seen by the user. In particular, the AR headset may capture an image of what is being viewed by the user and can generate augmented reality images to overlay on top of the image. For example, the user may specify objects or content to be blocked by the AR headset to achieve a certain goal.

In these aspects of the present disclosure, as images are captured by the AR headset, advanced semantic segmentation of images, audio analysis, and/or other media processing is used to identify the specified objects. The AR headset may then block or modify the identified objects as seen by the user through the AR headset, for example, as shown in FIG. 4.

Figure 4:
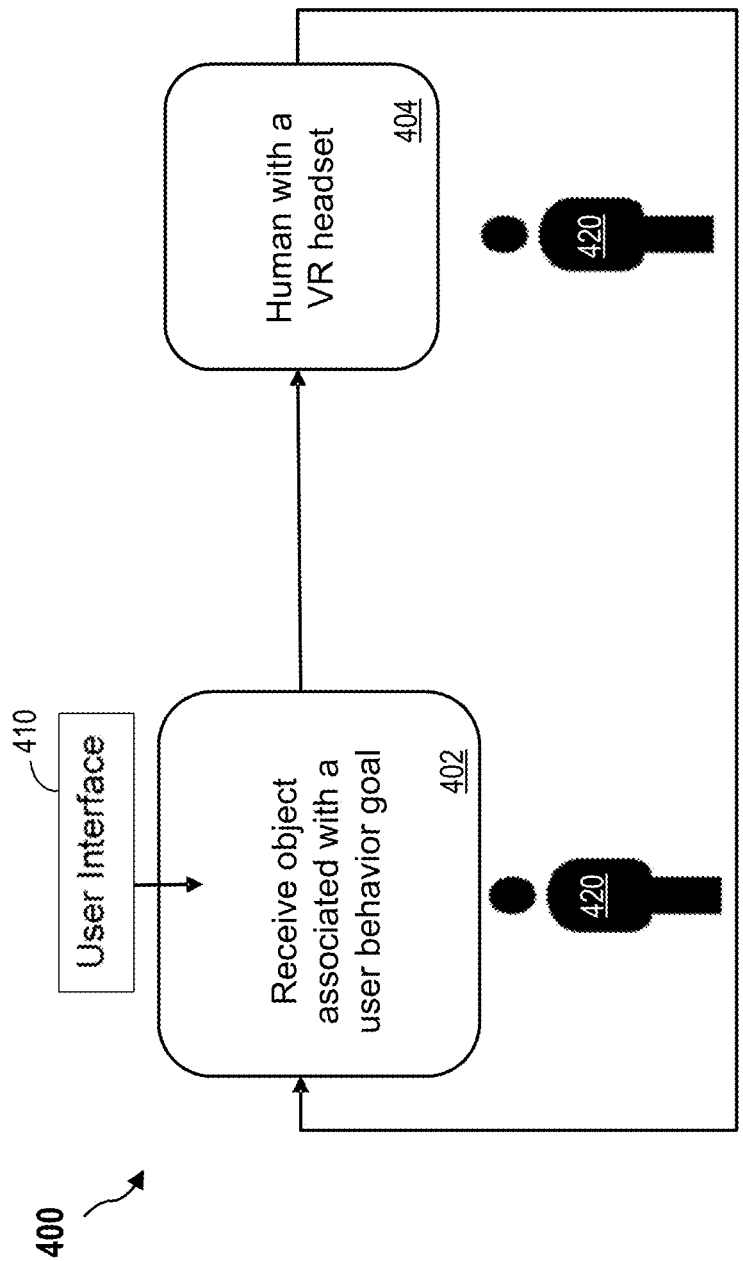
FIG. 4 is a block diagram illustrating an interaction method of an augmented reality goal assistance system, in accordance with aspects of the present disclosure.

FIG. 4 is a block diagram illustrating an interaction method of an augmented reality goal assistance system, in accordance with aspects of the present disclosure. A method 400 begins a block 402, in which a user 420 accesses a web application interface 410 (e.g., a user interface) to highlight types of everyday objects that should be highlighted or hidden. At block 404, the user 420 wears an augmented reality headset, which automatically highlights or hides the relevant everyday objects. The following use cases are possible examples of the augmented reality goal assistance system.

In a first use case (e.g., use case 1), Spendy Spencer wants to save money for a down payment on a house but, unfortunately, Spencer likes to purchase expensive luxury watches. In this example, aspects of the present disclosure enable Spencer to attain his savings goal without having to expend willpower by directing Spencer to specify a time period and items related to his goal. In response, the system hides things that may cause Spencer to want to buy a watch (e.g., items unrelated to Spencer's goal). For example, the augmented reality goal assistant replaces the watches of people Spencer interacts with by an inexpensive string bracelet. In another example, the augmented reality goal assistant replaces items with advertisements for dog food (e.g., Spencer is a cat person). In a further example, the augmented reality goal assistant replaces audio advertisements for watches and luxury products with a voice that chants "A penny saved is a penny earned!" In another example, the augmented reality goal assistant replaces his local luxury watch store with a shop that specializes in artisanal grass-fed burgers (e.g., Spencer is vegetarian). As a result, Spencer might not see a single temptation throughout the time when he needs to save money, and will not need to use willpower to achieve his goal.

In a second use case (e.g., use case 2), Distracted Dahlia has a test coming up. Dahlia is an intelligent student who gets good grades when she studies, but unfortunately she is easily distracted by video games. Dahlia has decided that over the next couple of weeks, she uses the augmented reality goal assistant every evening from 6:00 pm to 9:00 pm. During the noted time period, Dahlia uses the augmented reality goal assistant to highlight study cues and downplay distracting cues. For example, the augmented reality goal assistance system causes her video game equipment to look gray and boring, or even blend into the background altogether. In addition, the augmented reality goal assistance system highlights Dahlia's study materials with a golden aura. When Dahlia looks in the direction, a voice whispers "come level up your knowledge of organic chemistry." In addition, if Dahlia is not studying, a nagging popup appears in her field of view prompting her to study.

In a third use case (e.g., use case 3), Healthy Harry desires eating more fruits and vegetables. Harry sets a daily target number of servings he desires to eat. Every time Harry walks by the office kitchen, a banner pops up that says "Eat 3 more to WIN BIG!" assuming he has 3 more servings to reach his goal. When he has reached his target number of servings, there is a virtual confetti explosion and celebratory music, plus a banner that tells Harry he wins "100 Health Bucks". Harry also requests the augmented reality goal assistance system to hide chocolate donuts, for which Harry has a particular weakness. In this example, the object identified by the user 420 is associated with a positive behavioral habit of the user 420.

Figure 5:
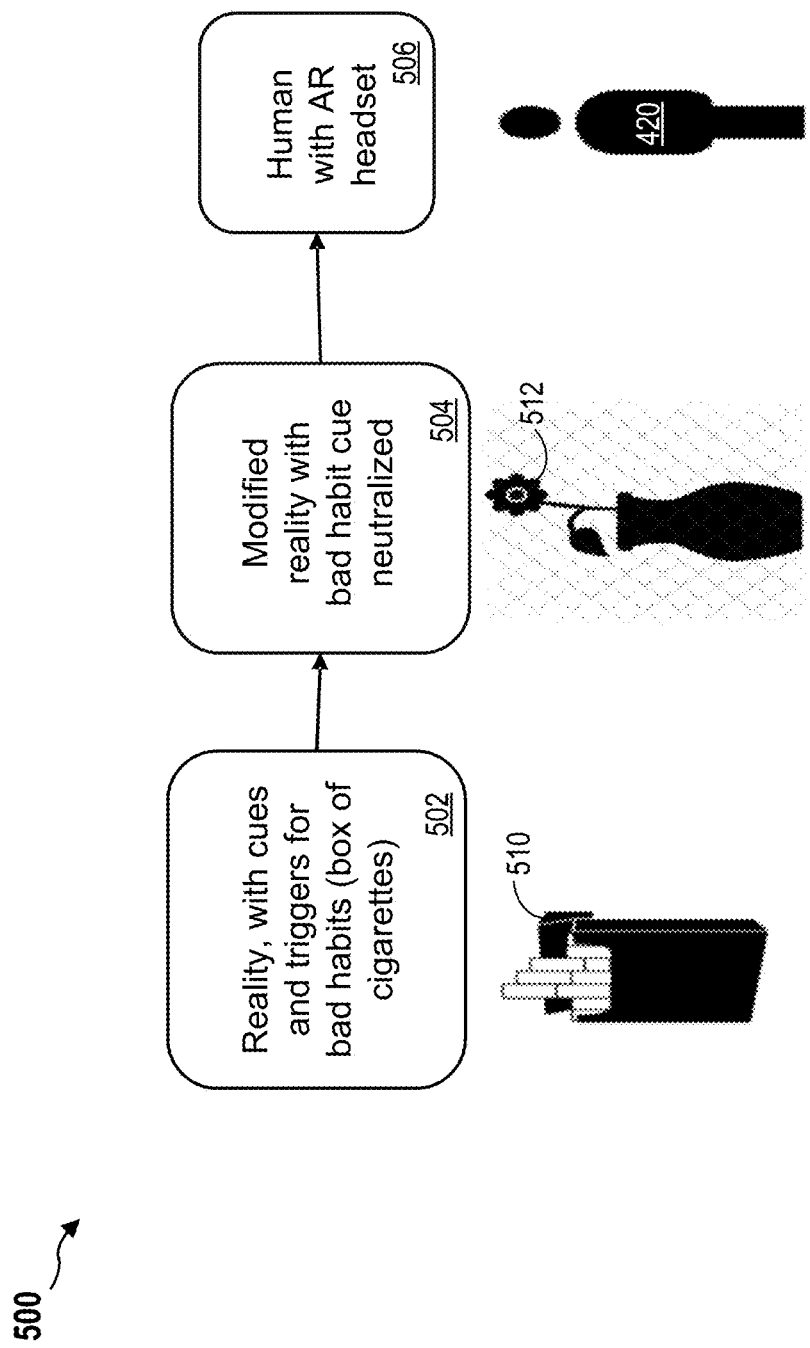
FIG. 5 is a block diagram further illustrating an augmented reality goal assistance system, in accordance with aspects of the present disclosure.

FIG. 5 is a block diagram further illustrating an augmented reality goal assistance process 500, in accordance with aspects of the present disclosure. In this example, the user 420 may specify that she wants to quit smoking cigarettes, which are shown at block 502. In this example, the user 420 identifies an object that is associated with a negative behavioral habit of the user 420. At block 502, reality is shown with cues and triggers for bad behavior, such as a box of the cigarettes 510. At block 504, an AR headset may create AR images, and overlay the AR images when the user 420 looks at the box of cigarettes 510. In this example, at block 504, reality is modified with the bad habit cue neutralized by displaying an AR image of a flower 512 over the box of cigarettes. Accordingly, at block 506, when the user 420 looks at the box of cigarettes 510, the AR headset replaces the box of cigarettes with the flower 512 in order to prevent the user 420 from being tempted by the box of cigarettes 510. An augmented reality goal assistance system may engage in a process, for example, as shown in FIG. 6.

Figure 6:
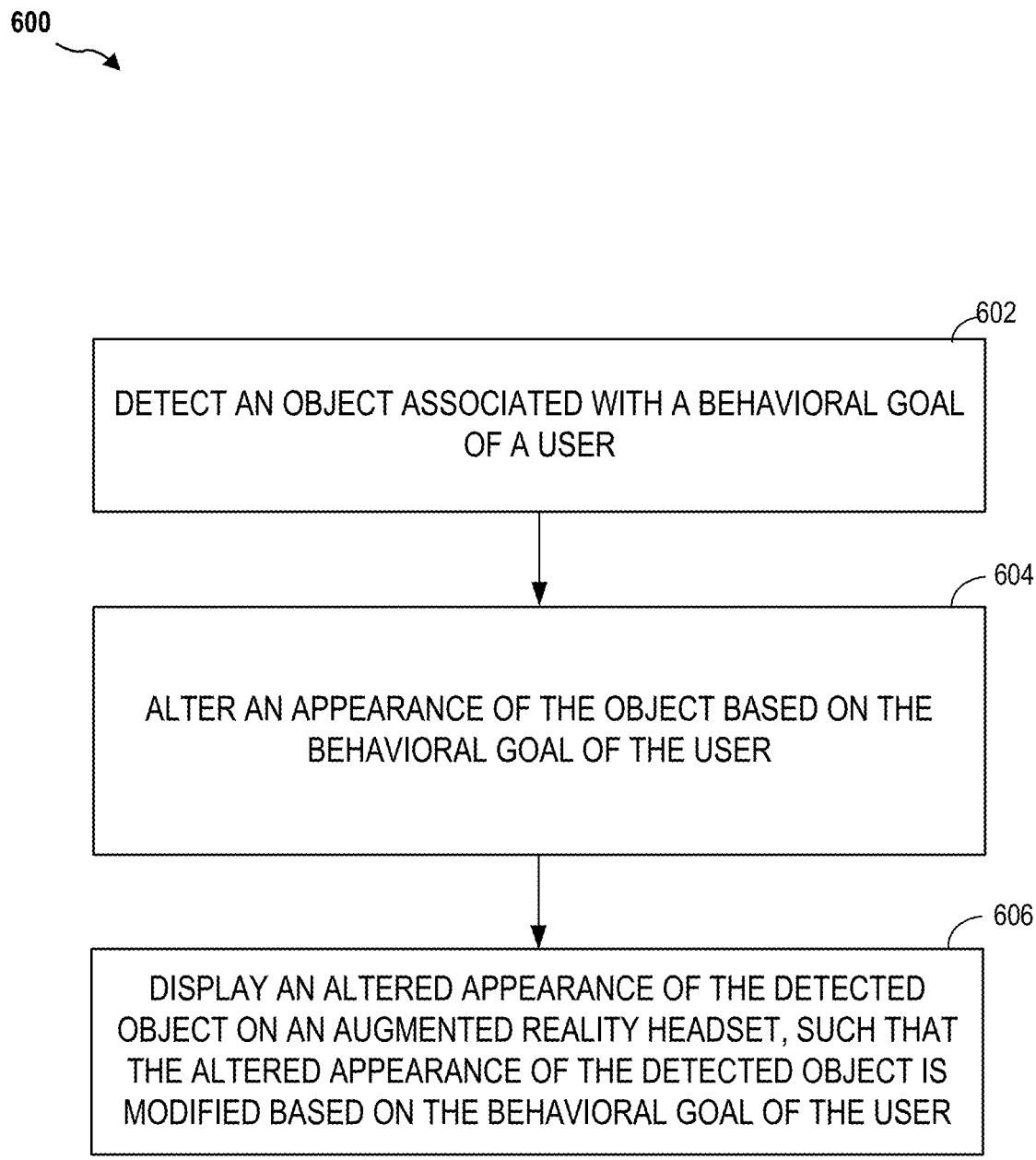
FIG. 6 is a flowchart illustrating a method for augmented reality goal assistance, according to aspects of the present disclosure.

FIG. 6 is a flowchart illustrating a method for an augmented reality goal assistant, according to aspects of the present disclosure. A method 600 of FIG. 6 begins at block 602, in which an object associated with a behavioral goal of a user is detected. For example, as shown in FIG. 4, the user 420 accesses the web application interface 410 (e.g., a user interface) to highlight types of everyday objects that should be highlighted or hidden. As described in FIG. 5, at block 502, reality is shown with cues and triggers for bad behavior, such as the box of the cigarettes 510. In this example, the user 420 specifies that she wants to quit smoking cigarettes, which are shown at block 502.

Referring again to FIG. 6, at block 604, an appearance of the object is altered based on the behavioral goal of the user. For example, as shown in FIG. 5, At block 504, an AR headset may create AR images, and overlay the AR images when the user 420 looks at the box of cigarettes 510. In this example, at block 504, reality is modified with the bad habit cue neutralized by displaying an AR image of a flower 512 over the box of cigarettes.

At block 606, an altered appearance of the detected object is displayed on an augmented reality headset, such that the altered appearance of the detected object is modified based on the behavioral goal of the user. For example, as shown in FIG. 4, at block 404, the user 420 wears an augmented reality headset, which automatically highlights or hides the relevant everyday objects. As shown in FIG. 5, at block 506, when the user 420 looks at the box of cigarettes 510, the AR headset replaces the box of cigarettes with the flower 512 in order to prevent the user 420 from being tempted by the box of cigarettes 510.

The method 600 may also include displaying by generating a pop-up message. The method 600 may also include playing audio of the pop-up message to remind the user to perform a positive behavioral habit of the user. The method 600 may also include displaying by replacing the detected object with an undesirable object if the detected object is associated with a negative behavioral habit of the user.

In these aspects of the present disclosure, as images are captured by the AR headset, advanced semantic segmentation of images, audio analysis, and/or other media processing is used to identify the specified objects. The AR headset may then block or modify the identified objects as seen by the user through the AR headset. For example, a user may specify that she does not want to play video games during a certain time period. Accordingly, during this time period, the AR headset may create AR images such that when the user looks at her video game system, it looks unappealing or it blends into the background. In another example, a user may specify that he wants to save money for a house and not spend it on expensive watches. Accordingly, when the user looks at an expensive watch, the AR headset may replace it with a string bracelet or other inexpensive object in order to prevent the user from getting excited about buying a similar watch. In other examples, a user may specify objects to highlight or accentuate. For example, a user may have a goal of eating more healthy food such as fruits and vegetables. Accordingly, whenever the user looks at fruits and vegetables, the AR headset may display a pleasing image or a message encouraging him to eat the fruits and vegetables. The AR headset may also block out unhealthy foods specified by the user such as chocolate donuts.

The various operations of methods described above may be performed by any suitable means capable of performing the corresponding functions. The means may include various hardware and/or software component(s) and/or module(s), including, but not limited to, a circuit, an application-specific integrated circuit (ASIC), or processor. Generally, where there are operations illustrated in the figures, those operations may have corresponding counterpart means-plus-function components with similar numbering.

As used herein, the term "determining" encompasses a wide variety of actions. For example, "determining" may include calculating, computing, processing, deriving, investigating, looking up (e.g., looking up in a table, a database or another data structure), ascertaining, and the like. Additionally, "determining" may include receiving (e.g., receiving information), accessing (e.g., accessing data in a memory), and the like. Furthermore, "determining" may include resolving, selecting, choosing, establishing, and the like.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logical blocks, modules and circuits described in connection with the present disclosure may be implemented or performed with a processor configured according to the present disclosure, a digital signal processor (DSP), an ASIC, a field-programmable gate array signal (FPGA) or other programmable logic device (PLD), discrete gate or transistor logic, discrete hardware components, or any combination thereof designed to perform the functions described herein. The processor may be a microprocessor, but, in the alternative, the processor may be any commercially available processor, controller, microcontroller, or state machine specially configured as described herein. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the present disclosure may be embodied directly in hardware, in a software module executed by a processor, or in a combination of the two. A software module may reside in any form of storage medium that is known in the art. Some examples of storage media that may be used include random access memory (RAM), read-only memory (ROM), flash memory, erasable programmable read-only memory (EPROM), electrically erasable programmable read-only memory (EEPROM), registers, a hard disk, a removable disk, a CD-ROM, and so forth. A software module may comprise a single instruction, or many instructions, and may be distributed over several different code segments, among different programs, and across multiple storage media. A storage medium may be coupled to a processor such that the processor can read information from, and write information to, the storage medium. In the alternative, the storage medium may be integral to the processor.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

The functions described may be implemented in hardware, software, firmware, or any combination thereof If implemented in hardware, an example hardware configuration may comprise a processing system in a device. The processing system may be implemented with a bus architecture. The bus may include any number of interconnecting buses and bridges depending on the specific application of the processing system and the overall design constraints. The bus may link together various circuits including a processor, machine-readable media, and a bus interface. The bus interface may connect a network adapter, among other things, to the processing system via the bus. The network adapter may implement signal processing functions. For certain aspects, a user interface (e.g., keypad, display, mouse, joystick, etc.) may also be connected to the bus. The bus may also link various other circuits such as timing sources, peripherals, voltage regulators, power management circuits, and the like, which are well known in the art, and therefore, will not be described any further.

The processor may be responsible for managing the bus and processing, including the execution of software stored on the machine-readable media. Examples of processors that may be specially configured according to the present disclosure include microprocessors, microcontrollers, DSP processors, and other circuitry that can execute software. Software shall be construed broadly to mean instructions, data, or any combination thereof, whether referred to as software, firmware, middleware, microcode, hardware description language, or otherwise. Machine-readable media may include, by way of example, RAM, flash memory, ROM, programmable read-only memory (PROM), EPROM, EEPROM, registers, magnetic disks, optical disks, hard drives, or any other suitable storage medium, or any combination thereof. The machine-readable media may be embodied in a computer-program product. The computer-program product may comprise packaging materials.

In a hardware implementation, the machine-readable media may be part of the processing system separate from the processor. However, as those skilled in the art will readily appreciate, the machine-readable media, or any portion thereof, may be external to the processing system. By way of example, the machine-readable media may include a transmission line, a carrier wave modulated by data, and/or a computer product separate from the device, all which may be accessed by the processor through the bus interface. Alternatively, or in addition, the machine-readable media, or any portion thereof, may be integrated into the processor, such as the case may be with cache and/or specialized register files. Although the various components discussed may be described as having a specific location, such as a local component, they may also be configured in various ways, such as certain components being configured as part of a distributed computing system.

The processing system may be configured with one or more microprocessors providing the processor functionality and external memory providing at least a portion of the machine-readable media, all linked together with other supporting circuitry through an external bus architecture. Alternatively, the processing system may comprise one or more neuromorphic processors for implementing the neuron models and models of neural systems described herein. As another alternative, the processing system may be implemented with an ASIC with the processor, the bus interface, the user interface, supporting circuitry, and at least a portion of the machine-readable media integrated into a single chip, or with one or more FPGAs, PLDs, controllers, state machines, gated logic, discrete hardware components, or any other suitable circuitry, or any combination of circuits that can perform the various functions described throughout this present disclosure. Those skilled in the art will recognize how best to implement the described functionality for the processing system depending on the particular application and the overall design constraints imposed on the overall system.

The machine-readable media may comprise a number of software modules. The software modules include instructions that, when executed by the processor, cause the processing system to perform various functions. The software modules may include a transmission module and a receiving module. Each software module may reside in a single storage device or be distributed across multiple storage devices. By way of example, a software module may be loaded into RAM from a hard drive when a triggering event occurs. During execution of the software module, the processor may load some of the instructions into cache to increase access speed. One or more cache lines may then be loaded into a special purpose register file for execution by the processor. When referring to the functionality of a software module below, it will be understood that such functionality is implemented by the processor when executing instructions from that software module. Furthermore, it should be appreciated that aspects of the present disclosure result in improvements to the functioning of the processor, computer, machine, or other system implementing such aspects.

If implemented in software, the functions may be stored or transmitted over as one or more instructions or code on a non-transitory computer-readable medium. Computer-readable media include both computer storage media and communication media, including any medium that facilitates transfer of a computer program from one place to another. A storage medium may be any available medium that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Additionally, any connection is properly termed a computer-readable medium. For example, if the software is transmitted from a website, server, or other remote source using a coaxial cable, fiber optic cable, twisted pair, digital subscriber line (DSL), or wireless technologies such as infrared (IR), radio, and microwave, then the coaxial cable, fiber optic cable, twisted pair, DSL, or wireless technologies such as infrared, radio, and microwave are included in the definition of medium. Disk and disc, as used herein, include compact disc (CD), laser disc, optical disc, digital versatile disc (DVD), floppy disk, and Blu-ray® disc where disks usually reproduce data magnetically, while discs reproduce data optically with lasers. Thus, in some aspects computer-readable media may comprise non-transitory computer-readable media (e.g., tangible media). In addition, for other aspects, computer-readable media may comprise transitory computer-readable media (e.g., a signal). Combinations of the above should also be included within the scope of computer-readable media.

Thus, certain aspects may comprise a computer program product for performing the operations presented herein. For example, such a computer program product may comprise a computer-readable medium having instructions stored (and/or encoded) thereon, the instructions being executable by one or more processors to perform the operations described herein. For certain aspects, the computer program product may include packaging material.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a CD or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes, and variations may be made in the arrangement, operation, and details of the methods and apparatus described above without departing from the scope of the claims.

What is claimed is:

1. A method for an augmented reality goal assistant, comprising:
   detecting an object associated with a behavioral goal of a user;
   altering an appearance of the object based on the behavioral goal of the user;
   displaying the altered appearance of a detected object on an augmented reality headset, such that the altered appearance of the detected object is modified based on the behavioral goal of the user;
   modifying the appearance of the detected object to form the detected object in an undesired state as an undesirable object; and
   replacing the detected object with the undesirable object if the detected object is associated with a negative behavioral habit of the user.

2. The method of claim 1, in which detecting comprises:
recognizing the object; and
determining a recognized object is associated with the behavioral goal of the user.

3. The method of claim 2, in which the object is associated with a positive behavioral habit of the user.

4. The method of claim 1, in which the object is associated with a negative behavioral habit of the user.

5. The method of claim 1, in which displaying comprises obscuring the detected object if the detected object is associated with a negative behavioral habit of the user.

6. The method of claim 1, in which displaying comprises enhancing the detected object if the detected object is associated with a positive behavioral habit of the user.

7. The method of claim 1, in which displaying further comprises:
generating a pop-up message; and
playing audio of the pop-up message to remind the user to perform a positive behavioral habit of the user.

8. A non-transitory computer-readable medium having program code recorded thereon for an augmented reality goal assistant, the program code being executed by a processor and comprising:
program code to detect an object associated with a behavioral goal of a user;
program code to alter an appearance of the object based on the behavioral goal of the user;
program code to display the altered appearance of a detected object on an augmented reality headset, such that the altered appearance of the detected object is modified based on the behavioral goal of the user; and
program code to modify the appearance of the detected object to form the detected object in an undesired state as an undesirable object; and
program code to replace the detected object with the undesirable object if the detected object is associated with a negative behavioral habit of the user.

9. The non-transitory computer-readable medium of claim 8, in which the program code to detect comprises:
program code to recognize the object; and
program code to determine a recognized object is associated with the behavioral goal of the user.

10. The non-transitory computer-readable medium of claim 9, in which the object is associated with a positive behavioral habit of the user.

11. The non-transitory computer-readable medium of claim 8, in which the object is associated with a negative behavioral habit of the user.

12. The non-transitory computer-readable medium of claim 8, in which the program code to display comprises program code to obscure the detected object if the detected object is associated with a negative behavioral habit of the user.

13. The non-transitory computer-readable medium of claim 8, in which the program code to display comprises program code to enhance the detected object if the detected object is associated with a positive behavioral habit of the user.

14. The non-transitory computer-readable medium of claim 8, in which the program code to display further comprises:
program code to generate a pop-up message; and
program code to play audio of the pop-up message to remind the user to perform a positive behavioral habit of the user.

15. A system for an augmented reality goal assistant, comprising:
an object recognition module to detect an object associated with a behavioral goal of a user;
an object alteration module to alter an appearance of the object based on the behavioral goal of the user; and
an augmented reality display module to display the altered appearance of a detected object on an augmented reality headset, such that the altered appearance of the detected object is modified based on the behavioral goal of the user,
in which the object alteration module is further to modify the appearance of the detected object to form the detected object in an undesired state as an undesirable object; and
in which the augmented reality display module is further to replace the detected object with the undesirable object if the detected object is associated with a negative behavioral habit of the user.

16. The system of claim 15, in which the augmented reality display module is further configured to obscure the detected object if the detected object is associated with a negative behavioral habit of the user.

17. The system of claim 15, in which the augmented reality display module is further configured to enhance the detected object if the detected object is associated with a positive behavioral habit of the user.

18. The system of claim 15, in which the augmented reality display module is further configured:
to generate a pop-up message; and
to play audio of the pop-up message to remind the user to perform a positive behavioral habit of the user.

* * * * *